United States Patent
Kalbfeld et al.

(10) Patent No.: US 9,833,061 B2
(45) Date of Patent: Dec. 5, 2017

(54) DENTAL HYGIENE DEVICE

(71) Applicant: SUNSTAR AMERICAS, INC., Chicago, IL (US)

(72) Inventors: Russell G. Kalbfeld, Naperville, IL (US); Leoncio Angel Gonzalez, Winfield, IL (US)

(73) Assignee: SUNSTAR AMERICAS, INC., Schaumburg, IL (US)

( * ) Notice: Subject to any disclaimer, the term of this patent is extended or adjusted under 35 U.S.C. 154(b) by 0 days.

(21) Appl. No.: 14/853,312

(22) Filed: Sep. 14, 2015

(65) Prior Publication Data
US 2016/0000215 A1   Jan. 7, 2016

Related U.S. Application Data

(63) Continuation of application No. 13/103,866, filed on May 9, 2011, now Pat. No. 9,131,768.

(51) Int. Cl.
| | |
|---|---|
| *A46B 15/00* | (2006.01) |
| *A46B 17/00* | (2006.01) |
| *A46B 5/00* | (2006.01) |
| *A46B 5/02* | (2006.01) |
| *A61C 15/00* | (2006.01) |
| *A46B 3/18* | (2006.01) |

(52) U.S. Cl.
CPC ........ *A46B 15/0069* (2013.01); *A46B 5/0062* (2013.01); *A46B 5/02* (2013.01); *A46B 15/00* (2013.01); *A46B 17/00* (2013.01); *A61C 15/00* (2013.01); *A46B 3/18* (2013.01); *A46B 2200/108* (2013.01); *A46B 2200/1066* (2013.01)

(58) Field of Classification Search
CPC ... A46B 3/18; A46B 13/001; A46B 2200/108; A46B 5/007
USPC .................. 15/206, 207, 143.1, 144.1, 167.1
See application file for complete search history.

(56) References Cited

U.S. PATENT DOCUMENTS

| | | | |
|---|---|---|---|
| 376,540 | A | 1/1888 | McQuide |
| 759,490 | A | 5/1904 | Yates |

(Continued)

FOREIGN PATENT DOCUMENTS

| | | |
|---|---|---|
| DE | 519804 | 3/1931 |
| EP | 0 001 044 | 3/1979 |

(Continued)

OTHER PUBLICATIONS

Computer generated English translation of JP 2005-224268 A, Hidaka, Aug. 2005.*

(Continued)

*Primary Examiner* — Laura C Guidotti
(74) *Attorney, Agent, or Firm* — Michael Best & Friedrich LLP

(57) ABSTRACT

A dental hygiene device such as an interdental brush includes a handle, a brush head having bristles extending therefrom, and a neck portion extending between the brush head and the handle. The neck portion of the dental hygiene device is configured to provide two modes of operation, a first cleaning mode of operation wherein the brush head contacts the teeth at a first pressure for a given application pressure, and a second cleaning mode of operation wherein the brush head contacts the teeth at a second pressure, greater than the first pressure, for the same given application pressure.

7 Claims, 4 Drawing Sheets

(56) References Cited

U.S. PATENT DOCUMENTS

| | | |
|---|---|---|
| 1,369,966 A | 3/1921 | Cosens et al. |
| 1,465,522 A | 8/1923 | Lunday |
| 1,513,556 A | 10/1924 | Lucia |
| 1,806,520 A | 5/1931 | Cave |
| 1,894,413 A | 1/1933 | Nenning et al. |
| 1,963,360 A | 6/1934 | Gibbin et al. |
| 1,996,205 A | 4/1935 | Jackson |
| 2,094,240 A | 9/1937 | Herrick et al. |
| 2,164,219 A | 1/1939 | McGerry |
| 2,167,129 A | 7/1939 | Sleeper |
| 2,206,542 A | 7/1940 | Arnold |
| 2,319,841 A | 5/1943 | Bate |
| D157,514 S | 2/1950 | Perwas |
| D173,852 S | 1/1955 | Pope |
| 3,163,874 A | 1/1965 | Bauer |
| 3,204,275 A | 9/1965 | Baker |
| 3,559,226 A | 2/1971 | Burns |
| 3,720,975 A | 3/1973 | Nelson |
| 3,892,040 A | 7/1975 | Marquis |
| 4,030,199 A | 6/1977 | Russell |
| 4,222,143 A | 9/1980 | Tarrson et al. |
| 4,387,479 A | 6/1983 | Kigyos |
| 4,399,582 A | 8/1983 | Ernest et al. |
| D270,669 S | 9/1983 | Cassai et al. |
| 4,520,526 A | 6/1985 | Peters |
| 4,535,761 A | 8/1985 | Rabinowitz |
| 4,679,272 A | 7/1987 | Florence |
| 4,691,404 A | 9/1987 | Tarrson et al. |
| 4,829,621 A | 5/1989 | Phenegar |
| 5,351,358 A | 10/1994 | Larrimore |
| 5,377,377 A | 1/1995 | Bredall et al. |
| 5,488,751 A | 2/1996 | Gekhter et al. |
| 5,903,949 A | 5/1999 | Halm |
| D424,303 S | 5/2000 | Tobias |
| 6,101,659 A | 8/2000 | Halm |
| D445,958 S | 7/2001 | Dansreau et al. |
| 6,475,553 B2 | 11/2002 | Guay et al. |
| D538,046 S | 3/2007 | Tsaur |
| D587,846 S | 3/2009 | Wonderley et al. |
| 7,854,036 B2 | 12/2010 | Georgi |
| D635,716 S | 4/2011 | Rhoad |
| 8,567,000 B2 | 10/2013 | Kubo |
| 2001/0047556 A1 | 12/2001 | Weihrauch |
| 2003/0088932 A1 | 5/2003 | Gardiner |
| 2006/0179593 A1 | 8/2006 | Okamura |
| 2007/0086831 A1 | 4/2007 | Wold |
| 2008/0213731 A1 | 9/2008 | Fishburne |

FOREIGN PATENT DOCUMENTS

| | | | |
|---|---|---|---|
| FR | 671738 | 12/1929 | |
| JP | 63-3225 | 1/1988 | |
| JP | 63-3226 | 1/1988 | |
| JP | 6-70812 | 3/1994 | |
| JP | 2001204549 A | 7/2001 | |
| JP | 2004242781 A | 9/2004 | |
| JP | 2005-224268 A * | 8/2005 | ............... A46B 5/00 |
| JP | 3139202 U | 1/2008 | |
| KR | 10-0827549 B1 | 5/2008 | |
| WO | WO 2009/081783 A1 * | 7/2009 | ........... A46B 5/0062 |
| WO | 2010/038678 | 4/2010 | |

OTHER PUBLICATIONS

Computer generated English translation of WO 2009/081783 A1, Ohnishi, Jul. 2009.*
A Photograph of three Brushes by Sanyo-Hapics, Perio Pic, from Japan Perio Center, (date unknown).
Page 40 Oral Health, Jan. 1979.
Picture of unknown Japanese Brush (marked Exhibit AS1) of unknown date.
Denticator Brushes, (date unknown).
Photocopy of three Specimens, (marked Exhibit AT2), of unknown date.

* cited by examiner

DENTAL HYGIENE DEVICE

CROSS-REFERENCE TO RELATED APPLICATIONS

This patent application is a continuation of U.S. patent application Ser. No. 13/103,866, filed May 9, 2011, now U.S. Pat. No. 9,131,768. The above referenced application is hereby incorporated by reference.

BACKGROUND

An interdental brush is a dental hygiene device that can brush interdental spaces in the mouth. Interdental brushes typically include a handle and a brush head having a plurality of bristles that typically are constructed from short fibers. The brush head and bristles are sized and configured to be insertable into interdental spaces for cleaning thereof.

SUMMARY

In some aspects, an interdental brush includes a handle, a brush head having bristles extending therefrom, and a neck portion extending between the brush head and the handle. The neck portion defines a longitudinal axis and has a first bending stiffness when subject to loading in a first direction that is substantially perpendicular to the axis, and a second bending stiffness when subjected to loading in a second direction that is substantially perpendicular to the axis. The first bending stiffness being less than the second bending stiffness.

In other aspects, a neck for a dental hygiene device defines a longitudinal axis and includes a central portion formed of a first material, and a periphery portion extending along and adjacent to the central portion. The periphery portion is formed of a second material. The neck has a first bending stiffness when subject to loading in a first direction perpendicular to the axis and a second bending stiffness when subject to loading in a second direction perpendicular to the axis. The first bending stiffness is less than the second bending stiffness.

In other aspects, an interdental brush includes a handle and a neck portion extending from the handle and defining a longitudinal axis. A brush head includes bristles extending from the brush head in a plurality of radial directions, and at least some of the bristles have a substantially triangular cross section.

In other aspects the invention provides for an interdental brush for cleaning teeth, the interdental brush including a handle, a neck portion extending from the handle, and a brush head coupled to and extending from the neck portion, the brush head including a stem from which a plurality of bristles extend in a diametrically opposed manner. The neck portion being configured to provide two modes of operation, a first cleaning mode of operation where the brush head contacts the teeth at a first pressure for a given input pressure, and a second cleaning mode of operation where the brush head contacts the teeth at a second pressure, greater than the first pressure, for the same given input pressure.

In other aspects, an interdental brush includes a neck portion extending from the handle and having a first axis and a second axis, the neck portion having a first bending stiffness when subject to loading about the first axis, and a second bending stiffness when subject to loading about the second axis, the first bending stiffness being less than the second bending stiffness. The interdental brush also includes a brush head coupled to and extending from the neck portion, the brush head configured to be inserted into interdental spaces for cleaning thereof, and a handle, the handle having a first set of grips substantially aligned with the first axis of the neck portion and a second set of grips substantially aligned with the second axis.

Other aspects of the invention will become apparent by consideration of the detailed description and accompanying drawings.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

DETAILED DESCRIPTION

Figures 1, 5:
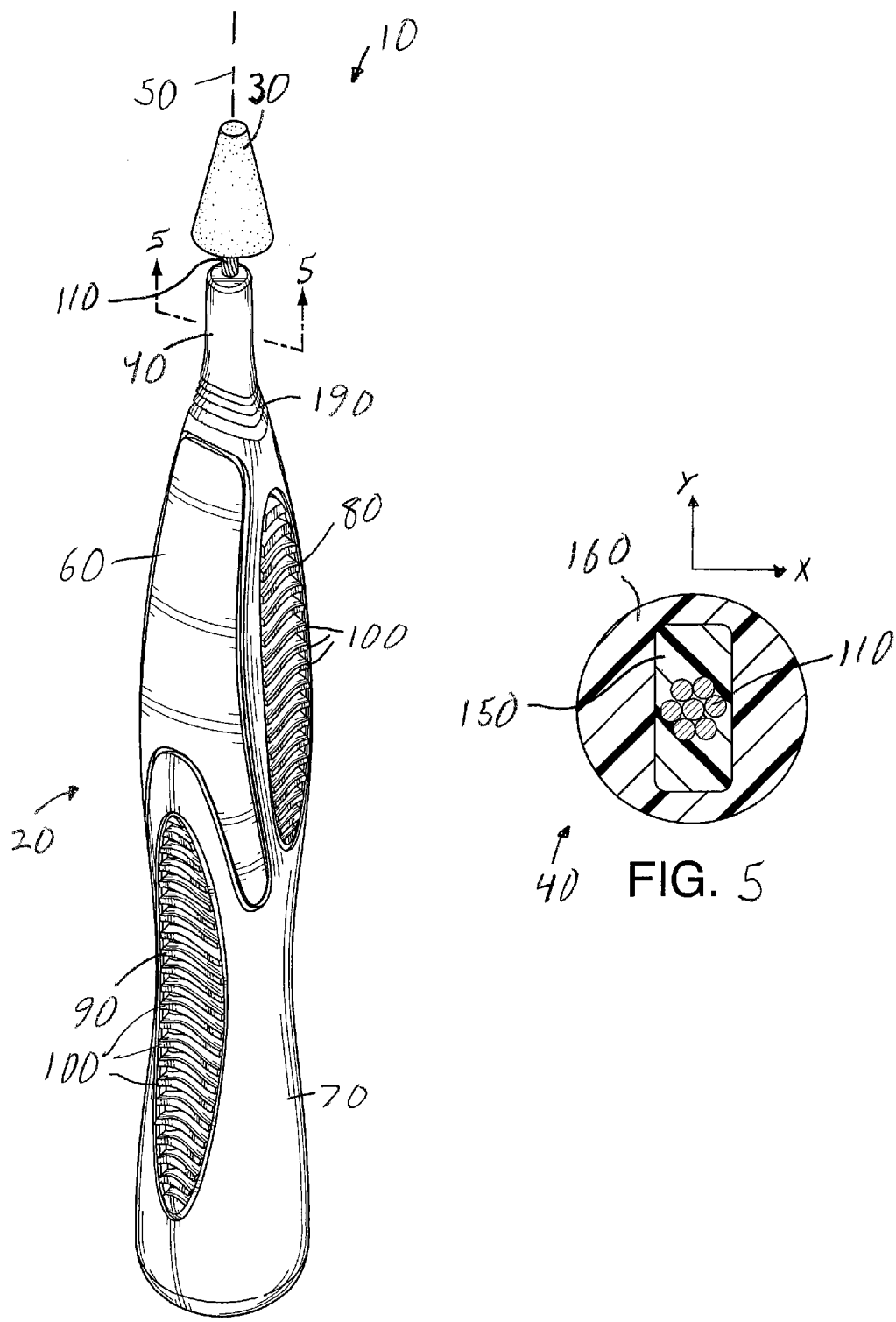
FIG. 1 is a perspective view of a dental hygiene device.
FIG. 5 is cross section view taken along line 5-5 of FIG. 1.

FIG. 1 is a perspective view of a dental hygiene device 10 in the form of an interdental brush. The device 10 includes a handle 20, a brush head 30, and an elongated neck 40 positioned between the handle 20 and the brush head 30. The neck 40 defines a longitudinal axis 50, and, in the illustrated construction, the handle 20 and the brush head 30 are substantially aligned with the longitudinal axis 50.

Figure 2:
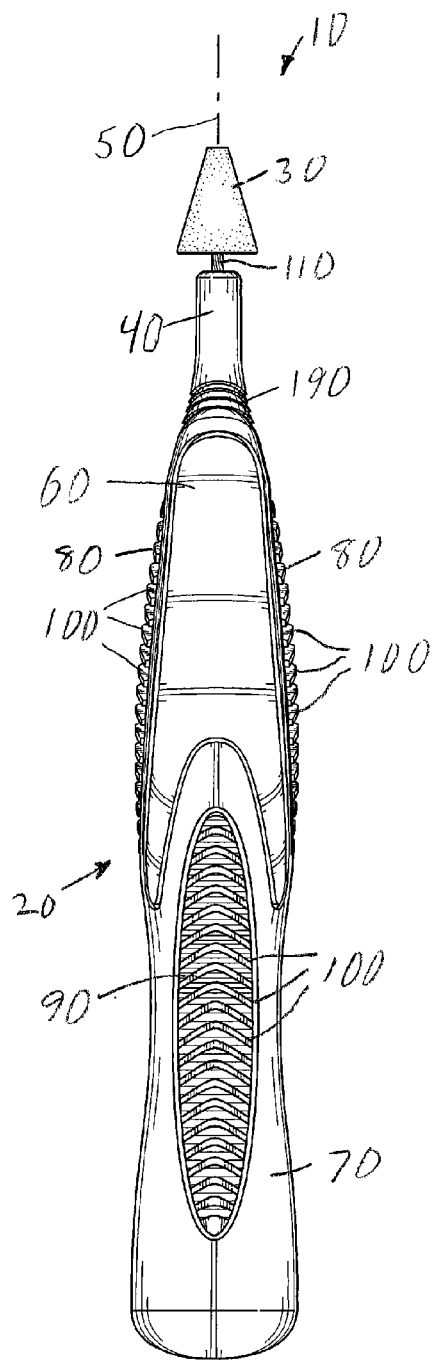
FIG. 2 is a side view of the dental hygiene device of FIG. 1
Figure 3:
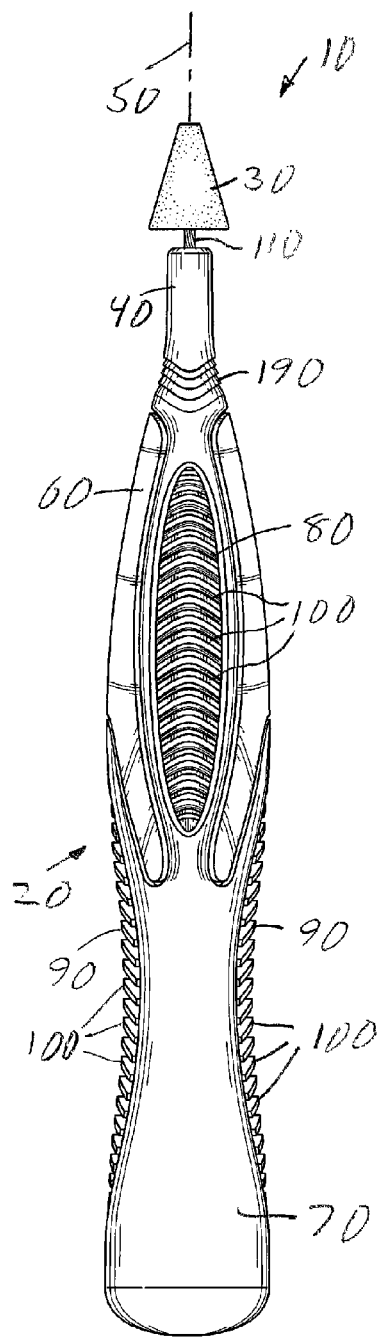
FIG. 3 is a front view of the dental hygiene device of FIG. 1.

Referring also to FIGS. 2 and 3, the handle 20 is generally hourglass-shaped, with bulbous upper and lower portions 60 and 70. In the illustrated embodiment, the upper portion 60 includes two tactily identifiable upper grip surfaces 80, and the lower portion 70 also includes two tactily identifiable lower grip surfaces 90. Each grip surface 80, 90 is substantially elliptical. The grip surfaces 80, 90 are positioned on opposite sides of the respective upper and lower portions 60, 70 of the handle 20. The upper and lower grip surfaces 80 and 90 are alternatingly arranged about the handle 20. In other words, if the handle 20 is divided into imaginary quadrants, the first and third quadrants each have a lower grip surface 90 but not an upper grip surface 80, and the second and fourth quadrant each have an upper grip surface 80 but not a lower grip surface 90. In one embodiment, the handle measures about 5.5 cm in length and about 0.7 cm in diameter.

With continuing reference to FIGS. 1-3, the upper and lower grip surface 80 and 90 are "louvered," including a plurality of fins or ribs or lateral slots 100. In the illustrated embodiment, the fins 100 are substantially chevron-shaped with the apex of each chevron pointing towards the brush head 30. In some embodiments, the fins 100 are evenly spaced along the handle 20 in a row. Furthermore, the fins 100 can be arranged such that they are angled away from the brush head 30. Leaning the fins 100 in this way can help keep debris from collecting between the fins 100, and can also improve a user's grip as the user inserts the brush head 30 into his or her interdental spaces.

The brush head 30 is mounted on the neck 40 by a bristle stem 110. In the illustrated construction, the bristle stem 110 comprises intertwined or braided wires, but can also be formed of a suitable polymeric or other material, or can be integrally formed with the handle 20 and/or neck 40. The bristle stem 110 can be secured in the neck 40 at a desired height using adhesive, fasteners, overmolding, insert molding, or any other suitable method. In the illustrated construction, the brush head 30 has a conical, domed, or pyramidal profile, with the apex of the brush head 30 pointing away from the bristle stem 110. The shape or profile of the brush head 30 is determined by the length and relative positioning of the filaments and/or fibers that make up individual bristles 120 of the brush head 30. Thus, for example, in other constructions the brush head 30 may be generally cylindrical, may include bristles 120 extending in a diametrically opposed manner from the bristle stem 110, may include bristles 120 arranged in a "cross" pattern when viewed along the axis, and may include bristles of varying lengths, thicknesses, and stiffnesses. Among other things, the size and shape of the bristles 120 and brush head 30 can vary according to the desired depth of penetration into the interdental spaces.

Figure 4:
FIG. 4 is a section view of a bristle of the dental hygiene device of FIG. 1.
Figure 6:
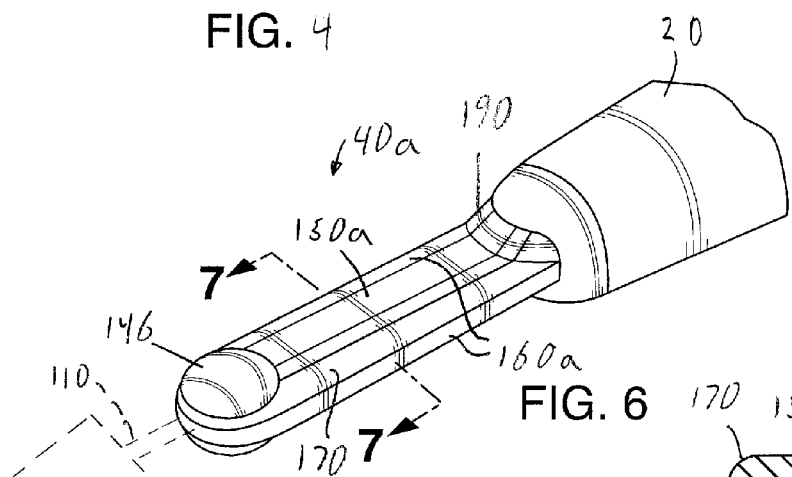
FIG. 6 is an enlarged perspective view, showing an alternative configuration for a neck portion of the dental hygiene device of FIG. 1.

Referring also to FIG. 4, at least some of the bristles 120 have a substantially triangular cross section. The triangular cross section of the bristles 120 has been found to enhance the cleaning effectiveness of the device 10. The cross section of each bristle 120 can be an equilateral, isosceles, or scalene triangle. In the illustrated embodiment, the triangular cross section of each bristle filament 120 includes rounded apexes 130. The filament 120 can be made of nylon or other suitable materials.

Referring to FIG. 5, the neck 40 is configured to be more elastically flexible in a first direction (e.g., the x-direction in FIG. 5) than it is in a second direction (e.g., the y-direction in FIG. 5). This variable flexibility is obtained by configuring the neck 40 to have a first bending stiffness when the brush head 30 is subjected to loading in the x-direction, and a second bending stiffness when the brush head 30 is subjected to loading in the y-direction, where the first bending stiffness is less than the second bending stiffness. For elongated beam-like structures such as the neck 40, the bending stiffness in any direction can be approximated using well known engineering equations derived from beam theory, and is generally a function of the modulus of elasticity E of the material(s) and the area moment of inertia I of the cross section. As used herein, the terms "flexible," "flexibility," and the like refer to elastic flexibility whereby when the structure in question is deflected away from a static position due to application of a load and that load is subsequently removed, the structure's inherent elasticity causes it to return more or less to the static position without any appreciable permanent deformation.

The neck 40 illustrated in FIG. 5 includes a central portion 150 formed of a first material having a first modulus of elasticity E1 and a generally rectangular cross section. In some constructions the first material is a polypropylene and may be the same material from which at least portions of the handle 20 are formed. In this regard, the central portion 150 may be integrally molded with certain portions of the handle 20. In other constructions, the central portion 150 may be coupled to the handle 20 using any suitable method. In the illustrated construction, the twisted or braided wires forming the bristle stem 110 are shown as being insert molded into the central portion 150. Other materials also may be used to form the central portion 150 and/or the handle 20, such as linear low density polyethylene, co-polyesters, or other suitable polymers.

A periphery portion 160 is adjacent to and surrounds the central portion 150. The periphery portion 160 is formed of a second material having a second modulus of elasticity E2 that is less than the modulus of elasticity E1. In some constructions, the second material is a thermoplastic elastomer that is overmolded onto the central portion, and may be the same material from which the grip surfaces 80, 90 are formed. In this regard, the periphery portion 160 may be overmolded onto the handle 20 and the central portion 150 during the same operation that overmolds the grip surfaces 80, 90 onto the handle 20. In the construction of FIG. 5, the periphery portion 160 is generally cylindrical with the exception of the central area that is occupied by the central portion 150. In other constructions, the periphery portion 160 may be coupled to the handle 20 and the central portion 150 in other suitable manners, such as by adhesives, sonic welding, or the like.

By way of example only, using the standard formula for calculating the area moment of inertia of a rectangular cross section ($I=(b*h^3)/12$, where b=the base of the rectangle and h=the height of the rectangle), the rectangular cross section of the central portion 150 provides an area moment of inertia Iy for bending moments about the y axis that is less than the area moment of inertia Ix for bending moments about the x axis. Similar results can be achieved by using a variety of different cross sections, such as an oval cross section, a diamond cross section, a properly selected I-beam cross section, a hollow-rectangular or oval cross section, and substantially any other cross section that results in different values for Iy and Ix. Although the periphery portion 160 of the construction illustrated in FIG. 5 also contributes to the bending stiffness of the neck 40, the majority of the overall bending stiffness of the neck 40 is established by the central portion 150 because of its larger modulus of elasticity E1. Some constructions of the device 10 may eliminate the periphery portion 160 in its entirety such that the bending stiffness of the neck 40 is determined solely by the central portion 150.

FIGS. 6-9 illustrate an alternative construction of the neck 40a that also achieves different bending stiffnesses in different directions. The neck 40a includes an elongated central portion 150a and a periphery portion 160a extending adjacent to the central portion 150a. Similar to the neck 40, the central portion 150a of the neck 40a is made of a first material having a modulus of elasticity that is greater than the modulus of elasticity of a second material that forms the periphery portion 160a. For example, the central portion 150a can be made of polymeric materials such as polypropylene, while the periphery portion 160a can be made of elastomeric materials such as thermoplastic elastomers. The central portion 150a can be integrally formed with the handle 20 or may be coupled to the handle 20 in a suitable manner. The periphery portion 160a can be over molded onto the central portion 150a, or may be attached to the handle 20 and central portion 150a using other suitable techniques.

In the neck 40a of FIGS. 6-9, certain surfaces of the central portion 150a and the periphery portion 160a are coplanar, such that portions of the central portion 150a remain exposed. The periphery portion 160a has rounded edges 170, so that the overall cross section of the neck 40a is generally rectangular with rounded corners (see FIG. 7). As shown, the central portion 150a is sandwiched between two portions of the periphery portion 160a, and a substantially ball-shaped tip 146 is formed from the second material. The rounded edges 170, ball-shaped tip 146, and softer thermoplastic elastomer materials (if used) can help provide a soft feeling to the gum tissue during use.

Figure 7:
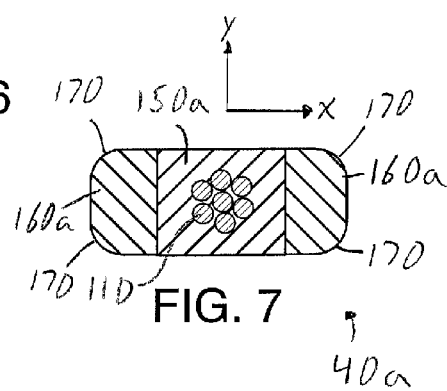
FIG. 7 is a section view taken along 7-7 of FIG. 6.
Figure 8:
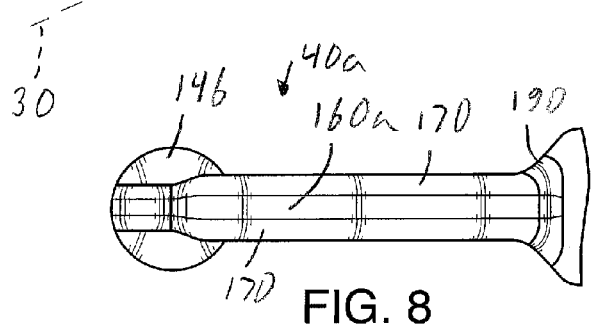
FIG. 8 is a side view of the neck portion of FIG. 6.
Figure 9:
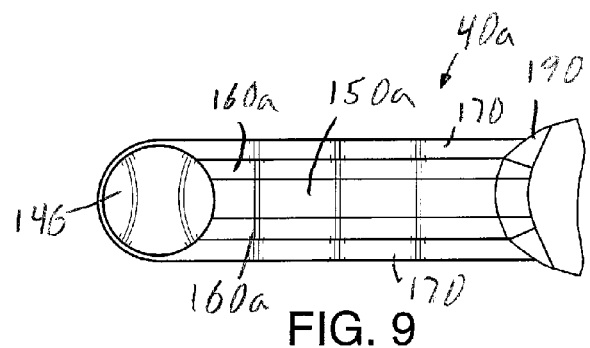
FIG. 9 is a front view of the neck portion of FIG. 6.

With reference to FIG. 7, the neck 40a is more flexible when subjected to bending in the y-direction than to bending in the x-direction because the overall cross section has different area moments of inertia Ix and Iy. Unlike the neck portion 40 of FIG. 5, where the difference in bending stiffness is attributable primarily to the structure of the central portion 150, the difference in bending stiffness of the neck portion 40a of FIG. 7 is attributable primarily to the selective positioning of the periphery portion 160a along only two sides of the central portion 150a. Thus, the area moment of inertia Iy of the periphery portion 160a is greater than the area moment of inertia Ix of the periphery portion 160a. As shown, the central portion 150a is square or nearly square, and therefore has area moments of inertia in about the x and y axes that are approximately the same. Positioning the periphery portion 160a along only two sides of the central portion more significantly increases the bending moment Iy of the overall cross section than the bending moment Ix of the overall cross section. The bristle stem 110 and brush head 30 (shown in phantom in FIG. 6) are coupled to and extend from the ball-shaped tip 146.

The configurations of the neck 40 of FIG. 5 and the neck 40a of FIGS. 6-9 are only two examples of possible neck constructions that provide the desired variation in bending stiffnesses in various directions. Other constructions are possible, including constructions configured to provide different bending stiffnesses in directions that are not necessarily perpendicular to one another as the x and y directions of FIGS. 5 and 7 are.

Figure 10:
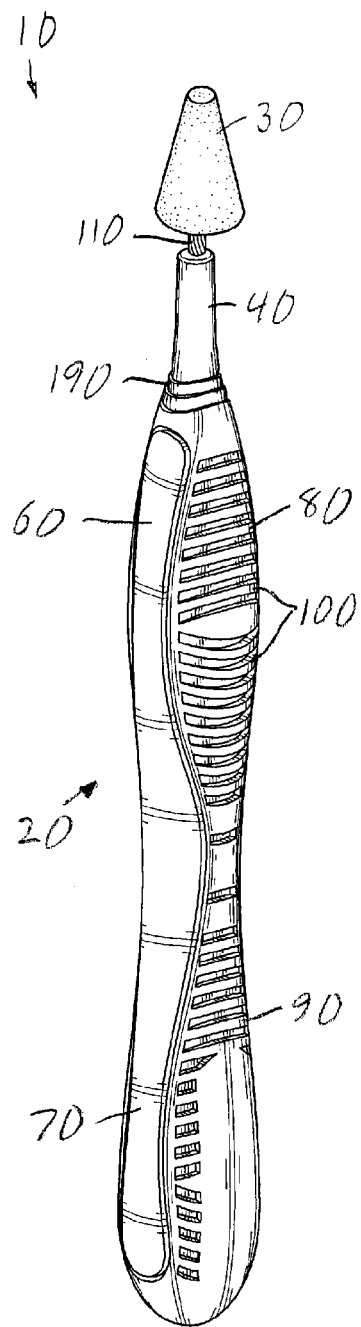
FIG. 10 is a perspective view of an alternative dental hygiene device.
Figure 11:
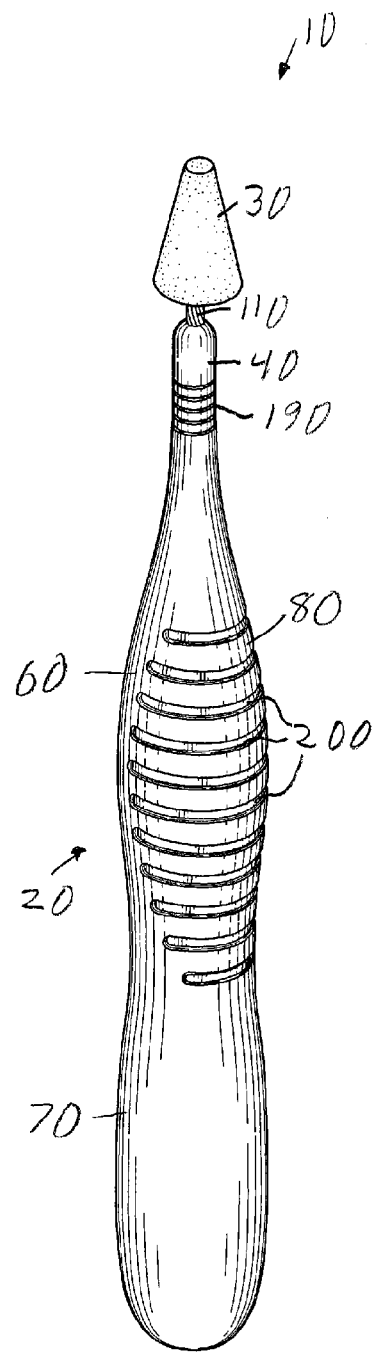
FIG. 11 is a perspective view of another alternative dental hygiene device.

FIGS. 10 and 11 illustrate alternative constructions of the handle 20, which can be used with either of the above-described neck portions 40 or 40a, or any of the various alternative constructions of the neck portions 40 or 40a described above. In the handle of FIG. 10, the upper and lower grip surfaces 80 and 90 are arranged on a same side of the handle 20. In other words, if the handle 20 is divided into successive imaginary quadrants about the axis 50, the first and third quadrants each have one or both of lower and upper grip surfaces 80, 90, and the second and fourth quadrant each have no upper or lower grip surfaces 80, 90. The upper and lower grip surfaces 80 and 90 may also be louvered with a plurality of fins or ribs 100 that are evenly spaced along the handle. The alternative handle 20 of FIG. 11, includes circumferentially-extending slots 200 extending various lengths around the upper portion 60. The slots 200 can be evenly spaced along the handle 20 and so dimensioned that as an aggregate, the resulting upper grip surface 80 is substantially elliptical in the plan view. In the various constructions, the neck portion 40 or 40a is coupled to the handle 20 by a transition portion 190. For example, the devices illustrated in FIGS. 1-3 and 10 include a transition portion 190 in the form of a tapered bellows structure, the device illustrated in FIGS. 6-9 includes a transition portion 190 in the form of a tapering radius structure, and the device illustrated in FIG. 11 includes a transition portion 190 with circumferential grooves that are evenly spaced from one another.

In each of the various constructions discussed above, the neck 40 or 40a can be oriented relative to the handle 20 such that the upper grip portion 80 is substantially aligned with one of the x-axis and the y-axis (see FIGS. 5 and 7) of the neck 40, 40a. In this way, when a user positions the brush head 30 against his or her gums, the user is able to tactily determine whether the device 10 is oriented in a direction that will present a greater or lesser bending stiffness in response to the application of pressure against the user's gums. Thus, using the neck configuration 40 of FIG. 5 as an example, if gentle cleaning is desired, the user can orient the device such that the y-axis is substantially parallel with the gum line. When the brush head 30 is pressed against the gum line in the direction of the x-axis, the neck 40 will relatively easily bend about the y-axis, thereby providing a soft, gentle cleaning. In contrast, if a more robust cleaning is desired, the user can orient the device such that the x-axis is substantially parallel with the gum line. When the brush head 30 is pressed against the gum line in the direction of the y-axis, the neck 40 will present greater resistance to bending, thereby provide a more vigorous, aggressive cleaning. The user can thereafter continue cleaning interdental spaces, orienting and reorienting the device as desired to provide a more gentle or more robust cleaning depending upon, for example, the sensitivity of the gum tissue in various locations of the mouth.

What is claimed is:

1. An interdental brush comprising:
   a neck portion extending from the handle and having a first axis and a second axis, the neck portion having a first bending stiffness when subject to loading about the first axis, and a second bending stiffness when subject to loading about the second axis, the first bending stiffness being less than the second bending stiffness;
   a brush head coupled to and extending from the neck portion, the brush head configured to be inserted into interdental spaces for cleaning thereof, wherein the brush head includes a plurality of bristles extending from a stem; and
   a handle, the handle having a first distinct set of grips substantially aligned with the first axis of the neck portion and a second distinct set of grips substantially aligned with the second axis, and
   wherein at least one bristle extends parallel to the first axis, and wherein at least one bristle extends parallel to the second axis.

2. The interdental brush of claim 1, further comprising a substantially ball-shaped tip portion positioned at an end of the neck and adjacent to the stem, the ball-shaped tip portion configured to provide a soft feeling to tissue adjacent the interdental spaces during use.

3. The interdental brush of claim 1, wherein the first axis is substantially perpendicular to the second axis.

4. The interdental brush of claim 1, wherein the first set of grips is tactilely distinct from the second set of grips.

5. The interdental brush of claim 1, wherein the brush head is substantially cylindrical in shape.

6. The interdental brush of claim 1, wherein the interdental brush is operable in a first mode of operation wherein pressing the brush head against the gums in a first direction presents a first level of resistance, and a second mode of operation wherein pressing the brush head against the gums in a second direction presents a second level of resistance, greater than the first level of resistance.

7. The interdental brush of claim 6, wherein a user grips the handle with the first set of grips when using the interdental brush in the first mode of operation, and wherein the user grips the handle with the second set of grips when using the interdental brush in the second mode of operation.

\* \* \* \* \*